United States Patent
Yamamoto et al.

(10) Patent No.: US 8,052,660 B2
(45) Date of Patent: Nov. 8, 2011

(54) LIQUID APPLICATOR FOR ENDOSCOPE

(75) Inventors: Akira Yamamoto, Tokyo (JP); Tetsuya Nakamura, Saitama (JP); Yae Kurosawa, Kanagawa (JP); Yusuke Iimori, Tokyo (JP); Pilryon Lee, Kanagawa (JP)

(73) Assignee: Hoya Corporation, Tokyo (JP)

( * ) Notice: Subject to any disclaimer, the term of this patent is extended or adjusted under 35 U.S.C. 154(b) by 245 days.

(21) Appl. No.: 11/610,081

(22) Filed: Dec. 13, 2006

(65) Prior Publication Data

US 2007/0135776 A1 Jun. 14, 2007

(30) Foreign Application Priority Data

Dec. 14, 2005 (JP) ................ P2005-360094

(51) Int. Cl.
*A61M 25/00* (2006.01)
*B43M 11/06* (2006.01)
*A61B 1/12* (2006.01)

(52) U.S. Cl. ........ 604/264; 600/156; 600/157; 600/159; 401/186

(58) Field of Classification Search .......... 604/264; 600/156–159; 401/186
See application file for complete search history.

(56) References Cited

U.S. PATENT DOCUMENTS

| | | | | |
|---|---|---|---|---|
| 2,729,505 A | * | 1/1956 | Harvey | 239/327 |
| 4,226,548 A | * | 10/1980 | Reith | 401/188 R |
| 4,838,722 A | * | 6/1989 | Katz | 401/101 |
| 4,932,094 A | * | 6/1990 | McCowin | 15/29 |
| 4,968,103 A | * | 11/1990 | McNab et al. | 300/21 |
| 5,240,675 A | * | 8/1993 | Wilk et al. | 422/22 |
| 5,408,991 A | * | 4/1995 | Iida et al. | 600/133 |
| 5,497,944 A |   | 3/1996 | Weston et al. | |
| 5,716,104 A | * | 2/1998 | Keating et al. | 300/21 |
| 5,788,628 A | * | 8/1998 | Matsuno et al. | 600/127 |
| 5,904,433 A | * | 5/1999 | Kay | 401/269 |
| 6,354,519 B1 | * | 3/2002 | Kidooka et al. | 239/491 |
| 6,745,427 B1 | * | 6/2004 | Trenz et al. | 15/104.94 |
| 7,204,824 B2 | * | 4/2007 | Moulis | 604/93.01 |
| 7,326,204 B2 | * | 2/2008 | Paul et al. | 606/41 |
| 2003/0032862 A1 |   | 2/2003 | Ota et al. | |
| 2003/0043264 A1 |   | 3/2003 | Furuya et al. | |
| 2003/0045779 A1 |   | 3/2003 | Ito | |
| 2006/0281973 A1 |   | 12/2006 | Sugita | |

FOREIGN PATENT DOCUMENTS

| | | |
|---|---|---|
| JP | 5-509241 | 12/1993 |
| JP | 6-70986 | 3/1994 |
| JP | 2001-104489 | 4/2001 |
| JP | 2001-137349 | 5/2001 |

OTHER PUBLICATIONS

English language Abstract of JP 6-70986.
English language Abstract of JP 2001-104489.
English language Abstract of JP 2001-137349.

* cited by examiner

*Primary Examiner* — Nicholas Lucchesi
*Assistant Examiner* — Ian Holloway
(74) *Attorney, Agent, or Firm* — Greenblum & Bernstein, P.L.C.

(57) ABSTRACT

A liquid applicator for an endoscope configured to apply liquid to in vivo tissue includes a flexible tube to be inserted into and extracted from a treatment tool insertion channel of the endoscope, a brush member provided at a distal end of the flexible tube, and a fluid channel formed in the flexible tube to supply the liquid to the brush member.

34 Claims, 9 Drawing Sheets

LIQUID APPLICATOR FOR ENDOSCOPE

BACKGROUND OF THE INVENTION

The present invention relates to a liquid applicator for an endoscope that is used in a manner inserted into a treatment tool insertion channel of the endoscope and configured to apply dye solution or medicinal solution to in vivo mucous membrane.

In an endoscope observation, it is possible, in some cases, to identify a condition of lesion that cannot be clarified in a usual endoscope observation by applying dye solution to in vivo mucous membrane. However, in such a method that the dye solution is conveyed with a catheter being inserted into a treatment tool insertion channel, it is undesired that a large amount of dye solution is caused to flow to a local portion, or that the dye solution is applied in the shape of waterdrop.

In order to solve this kind of problem, conventionally; a so-called spray tool for an endoscope that is configured to widely spray the dye solution in a human body has been employed (for example, see Japanese Patent Provisional Publications No. 2001-104489 and No. 2001-137349). Such a spray tool for an endoscope is used not only for spraying the dye solution, but also for spraying medicinal solution in the human body.

By observing a microscopically magnified image of the in vivo mucous membrane tissue using a confocal endoscope or other endoscopes having a so-called proximity magnification observation capability, it is possible to make a definite diagnosis about whether the in vivo mucous membrane tissue is a cancerous cell without taking the tissue. In such a case, a microscopic condition of the tissue can clearly be observed by applying the dye solution to a portion to be observed.

However, when spraying the dye solution into a stomach and intestines using the aforementioned spray tool for the endoscope, since the dye solution is caused to be sprayed to a wide area, the dye solution sometimes adheres to an observation port of the endoscope, and further it is impossible to confirm to which portion a cancerous cell found in the magnification observation corresponds after the observation has been completed. Accordingly, the dye solution is desired to be applied only to a small area of which a magnified image is to be observed.

In addition, since spraying the medicinal solution to a small lesioned part with the spray tool is similar to an undesired situation of applying an ointment to an entire arm to cure a damaged finger tip, it causes a need to consider side effects of the medicinal solution as well as a problem that a lot of medicinal solution is wasted.

SUMMARY OF THE INVENTION

The present invention is advantageous in that there can be provided an improved liquid applicator for an endoscope that is configured to accurately apply an appropriate amount of dye solution or medicinal solution to a small area inside a human body.

According to an aspect of the present invention, there is provided a liquid applicator for an endoscope configured to apply liquid to in vivo tissue, which includes: a flexible tube to be inserted into and extracted from a treatment tool insertion channel of the endoscope; a brush member provided at a distal end of the flexible tube; and a fluid channel formed in the flexible tube to supply the liquid to the brush member.

Optionally, the brush member may be formed with a plurality of pinfeathers being bundled, the brush member being attached to the distal end of the flexible tube to be protruded outward from the distal end of the flexible tube, the brush member being configured such that a distal end portion thereof can communicate with the fluid channel.

Optionally, the brush member may be configured such that a portion, protruded from the flexible tube, of each of the plurality of pinfeathers can independently bow.

Optionally, the brush member may be formed to have an external diameter smaller than that of the flexible tube.

Optionally, the brush member may include a hardened portion formed with the plurality of pinfeathers being fixed to each other in at least a portion of a part of the brush member to be attached to the distal end of the flexible tube, and a liquid passing opening that passes through the hardened portion along an axis line of the brush member.

Still optionally, an outer circumference of the hardened portion may be fixed to an inner circumference of the flexible tube.

Yet optionally, the brush member may be attached to the flexible tube without the hardened portion being protruded from the distal end of the flexible tube.

Optionally, the liquid applicator may further include a tubular pipe sleeve member attached to the distal end of flexible tube. In this case, an outer circumference of the hardened portion may be fixed to an inner circumference of the pipe sleeve member.

Further optionally, the pipe sleeve member may be fixed to the distal end of the flexible tube in a manner screwed thereinto.

Optionally, the brush member may be formed in a convergent tapered shape.

Optionally, the brush member may be pressed into the distal end of the flexible tube to be fixed thereto.

Still optionally, the brush member may be formed with the plurality of pinfeathers being arranged parallel to each other.

Further optionally, the liquid applicator may further include a convergent tapered core arranged on an axis line of a portion of the brush member located inside the flexible tube. Optionally, the brush member may be formed in a convergent tapered shape.

Optionally, the liquid applicator may further include a liquid storage portion provided at a rear anchor side of the flexible tube to pool the liquid to be conveyed to the fluid channel, the liquid storage portion communicating with the fluid channel in the flexible tube.

Further optionally, the liquid storage portion may be detachably provided at the rear anchor side of the flexible tube.

Optionally, the liquid storage portion may be formed in a pouched shape from resilient material. In this case, the liquid pooled in the liquid storage portion may be conveyed to the brush member via the fluid channel by applying a pressing force to the liquid storage portion from an outside thereof.

Furthermore, the liquid storage portion may be formed from rubber material.

Optionally, the flexible tube may be formed from ethylene tetrafluoride resin.

BRIEF DESCRIPTION OF THE ACCOMPANYING DRAWINGS

DETAILED DESCRIPTION OF THE EMBODIMENTS

Figure 6:
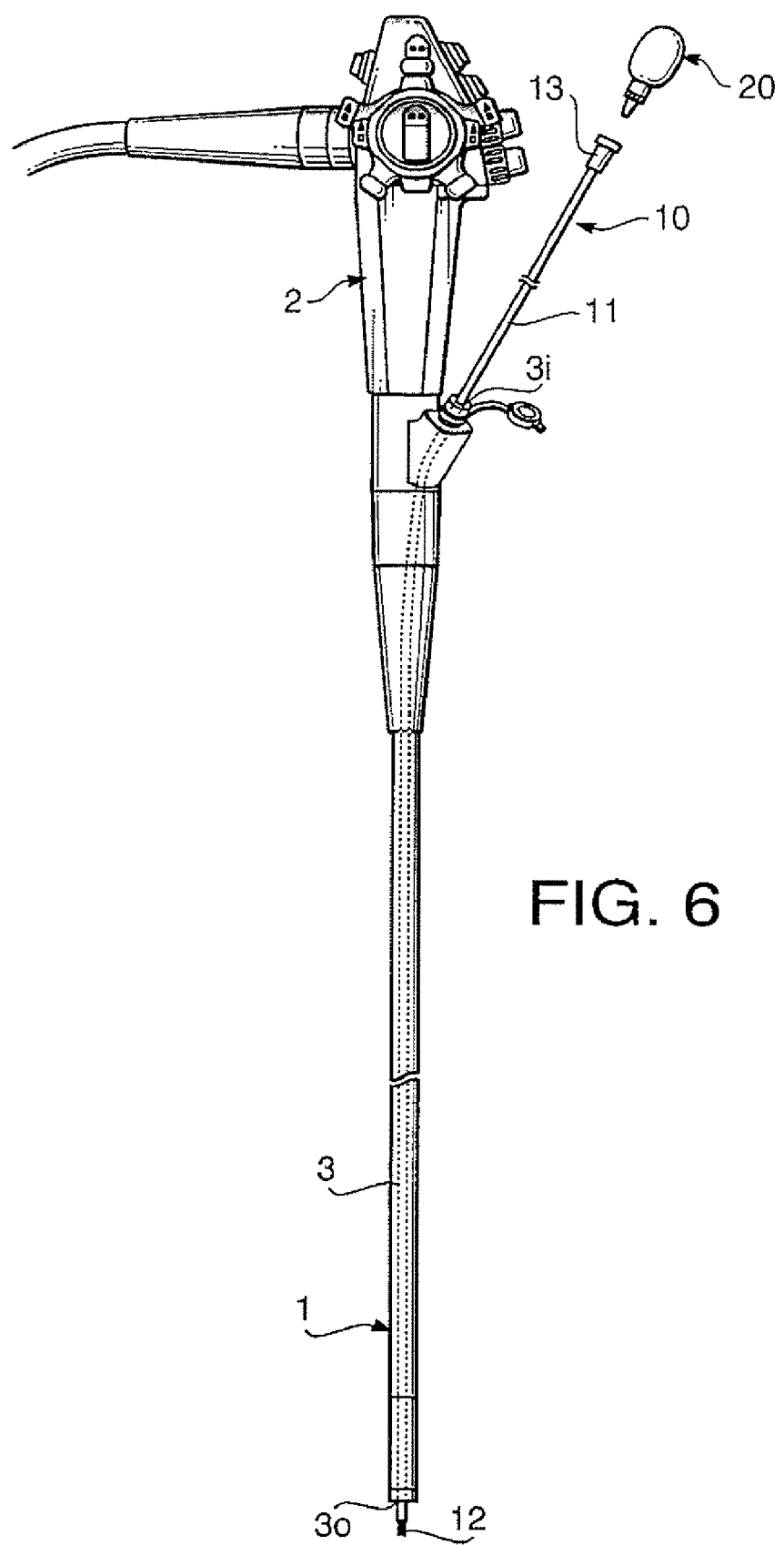
FIG. 6 shows an entire configuration of the distal end portion of the liquid applicator for the endoscope in use according to the first embodiment of the present invention.

Hereinafter, embodiments according to the present invention will be explained with reference to the accompanying drawings. FIG. 6 shows a state where a liquid applicator 10 for an endoscope according to the present invention is used. In FIG. 6, a reference sign 1 denotes an insertion part, and a reference sign 2 denotes an operating part. A liquid applicator 10 is used in a state of being inserted into a treatment tool insertion channel 3 provided over a whole length of the insertion part 1 of the endoscope, After use of the liquid applicator 10, it is extracted from the treatment tool insertion channel 3.

A flexible tube 11 that constitutes the liquid applicator 10 is formed longer than the treatment tool insertion channel 3 by one meter. The flexible tube 11 is used with a pinfeather bundle 12 attached to a distal end thereof being protruded from a treatment tool protrusion opening 3o at a distal end of the insertion part 1 of the endoscope. To a rear anchor portion of the flexible tube 11 extending from a treatment tool insertion opening 3i of the endoscope to an operator's hand side, there is attached a connection pipe sleeve 13 in the shape of an injection needle pipe sleeve, which is detachably connected with a liquid storage portion 20 filled with liquid such as dye solution and medicinal solution.

Figure 1:
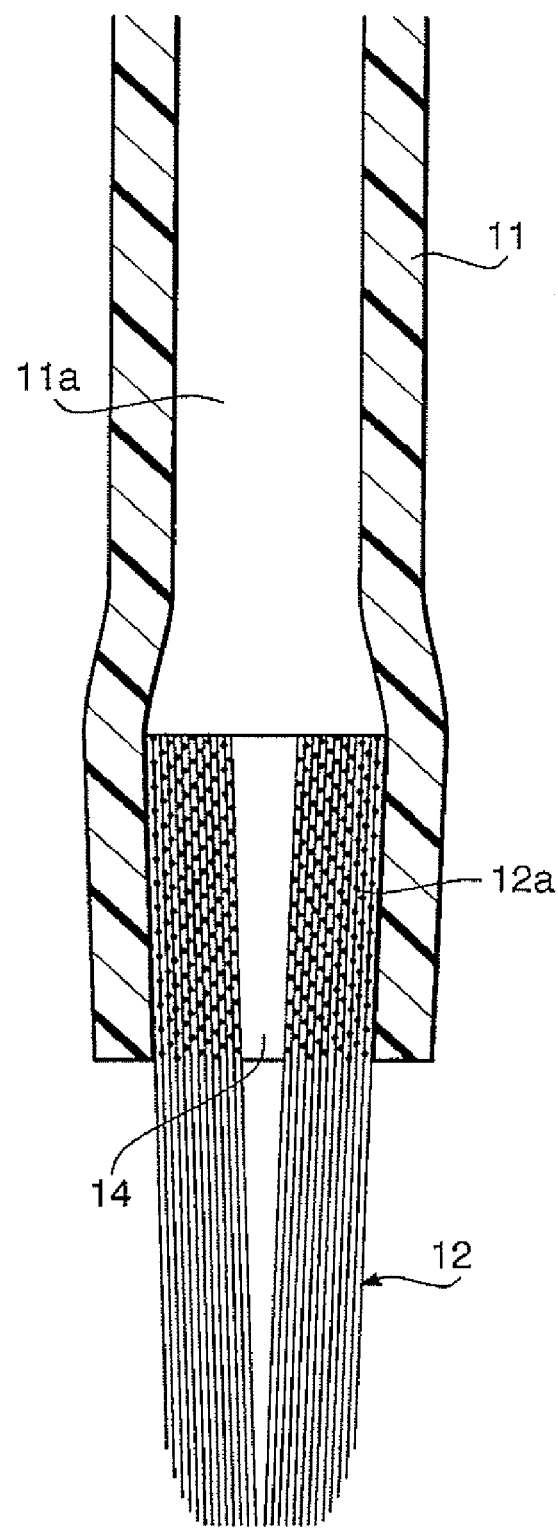
FIG. 1 is a cross-sectional side view of a distal end portion of a liquid applicator for an endoscope according to a first embodiment of the present invention.

FIG. 1 shows the distal end portion of the liquid applicator 10 according to a first embodiment of the present invention. The flexible tube 11 is, for example, formed with a tube made from ethylene tetrafluoride resin with a diameter of 2-3 mm and a wall thickness of 0.5-0.8 mm.

To a leading edge portion of the flexible tube 11, for example, there is attached the pinfeather bundle 12 formed with several hundreds of pinfeathers being bundled to be protruded outward from the distal end of the flexible tube 11. It is noted that the pinfeather bundle 12 may be formed with several tens of pinfeathers or more than thousand pinfeathers. The pinfeather bundle 12 is formed to have an external diameter smaller than that of the flexible tube 11 so that the pinfeather bundle 12 can smoothly pass through the treatment tool insertion channel 3.

Each of the pinfeathers forming the pinfeather bundle 12 is, for example, a thin flexible fiber with a diameter of 0.05-0.1 mm that has a restoring force that can restore itself to be straight, and may be made from highly biocompatible material such as polyamide resin and acrylic resin.

Figure 2:
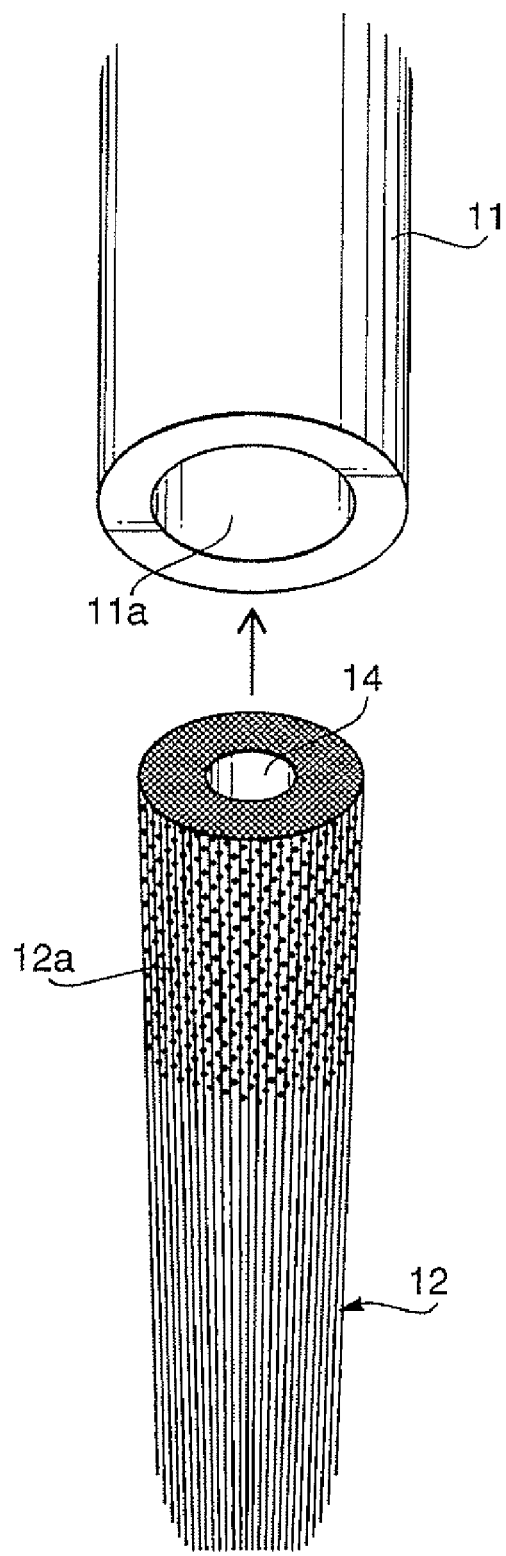
FIG. 2 is a perspective view of the distal end portion of the liquid applicator for the endoscope in process of assembling according to the first embodiment of the present invention.

As shown in FIG. 2 showing a state before being attached to the flexible tube 11, the pinfeather bundle 12 is arranged in a convergent tapered shape as a whole. A retracted portion of the pinfeather bundle 12 to be inserted into the distal end of the flexible tube 11 is hardened with adhesive material, and at the retracted portion, a number of pinfeathers are firmly fixed to each other. In each of the drawings, a portion denoted by black dots is a hardened portion 12a hardened with the adhesive material. A portion that is not to be inserted into the flexible tube 11 is not hardened.

As shown in FIGS. 1 and 2, a liquid passing opening 14 is formed around an axis line of the pinfeather bundle 12, and straightly communicates with a fluid channel 11a in the flexible tube 11. Since the pinfeather bundle 12 is formed in a convergent tapered shape, there are pinfeathers in the vicinity of a center of a leading edge portion of the pinfeather bundle 12.

The pinfeather bundle 12 is arranged such that each of the pinfeathers can independently bow at a portion protruded from the flexible tube 11 of the pinfeather bundle 12, and a distal end of the pinfeather bundle 12 communicates with the fluid channel 11a in the flexible tube 11.

The pinfeather bundle 12 is formed in a convergent tapered shape with the retracted hardened portion 12a of the pinfeather bundle 12 configured as above being inserted into the distal end of the flexible tube 11 and the leading edge portion of the flexible tube 11 being pressure-bonded to an outer circumference of the pinfeather bundle 12. Therefore, it is difficult to extract the pinfeather bundle 12 from the distal end of the flexible tube 11.

Further, an outer circumferential surface of the hardened portion 12a of the pinfeather 12 and an inner circumferential surface of the flexible tube 11 are firmly fixed to one another with adhesive material. Thereby, the pinfeather bundle 12 is more certainly prevented from being extracted from the distal end of the flexible tube 11. It is noted that the outer circumferential surface of the hardened portion 12a of the pinfeather 12 and the inner circumferential surface of the flexible tube 11 may not necessarily be adhered to one another.

Figure 3:
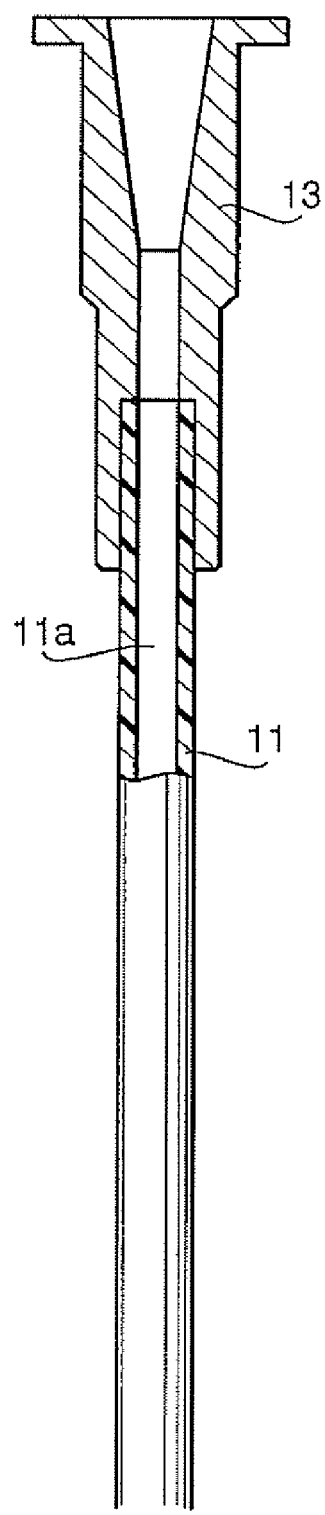
FIG. 3 is a cross-sectional side view of a rear anchor portion at an operator's hand side of the liquid applicator for the endoscope according to the first embodiment of the present invention.

FIG. 3 shows a rear anchor portion at an operator's hand side of the liquid applicator 10 for the endoscope. The connection pipe sleeve 13 attached to the rear anchor of the flexible tube 11 is, for example, a Lure-lock type injection needle pipe sleeve, and an inner channel thereof straightly communicates with the fluid channel 11a of the flexible tube 11.

Figure 4:
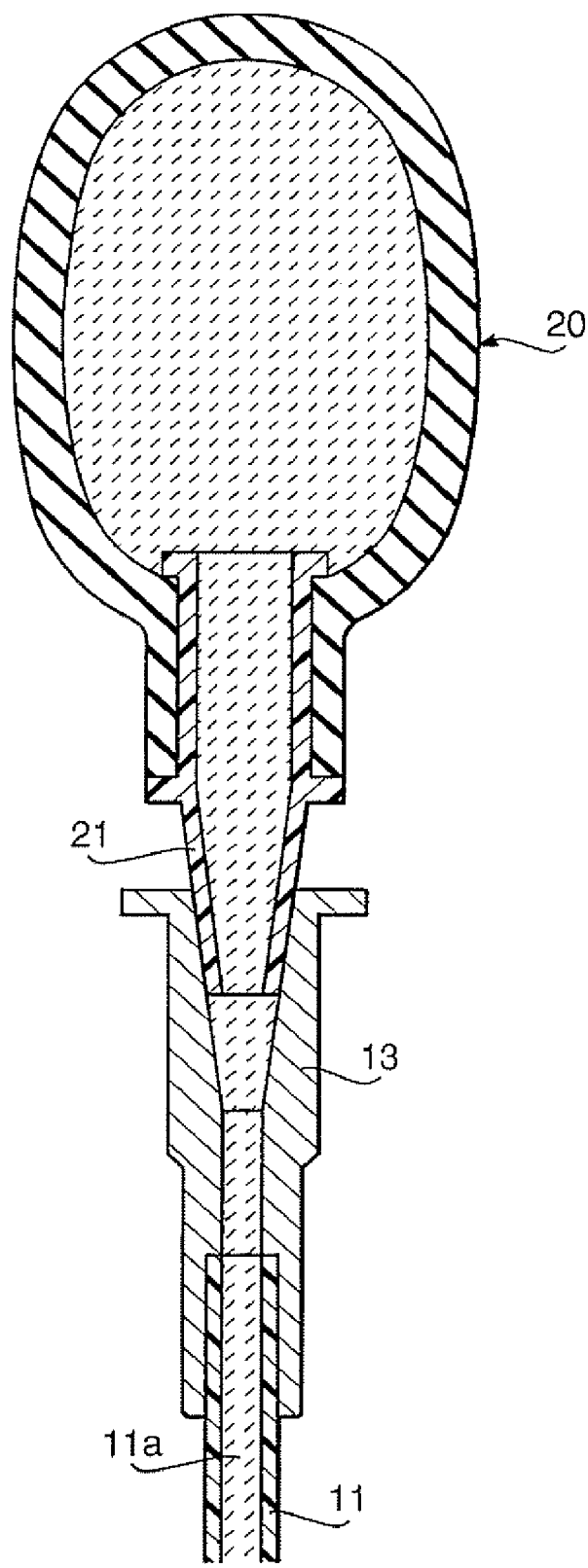
FIG. 4 is a cross-sectional side view of the rear anchor portion, to which a liquid storage portion is attached, at the operator's hand side of the liquid applicator for the endoscope according to the first embodiment of the present invention.

As shown in FIG. 4, the liquid storage portion 20 detachably connected with the connection pipe sleeve 13 is formed in a pouched shape from resilient rubber material, and only a distal end of a pipe sleeve 21 detachably engaged with the connection pipe sleeve 13 opens outward.

Accordingly, by applying a pressing force to the liquid storage portion 20 from an outside thereof the liquid in the liquid storage portion 20 is injected into the fluid channel 11a of the flexible tube 11. It is noted that any type of liquid storage portion may be employed as substitute for the liquid storage portion as shown in FIG. 4.

Figure 5:
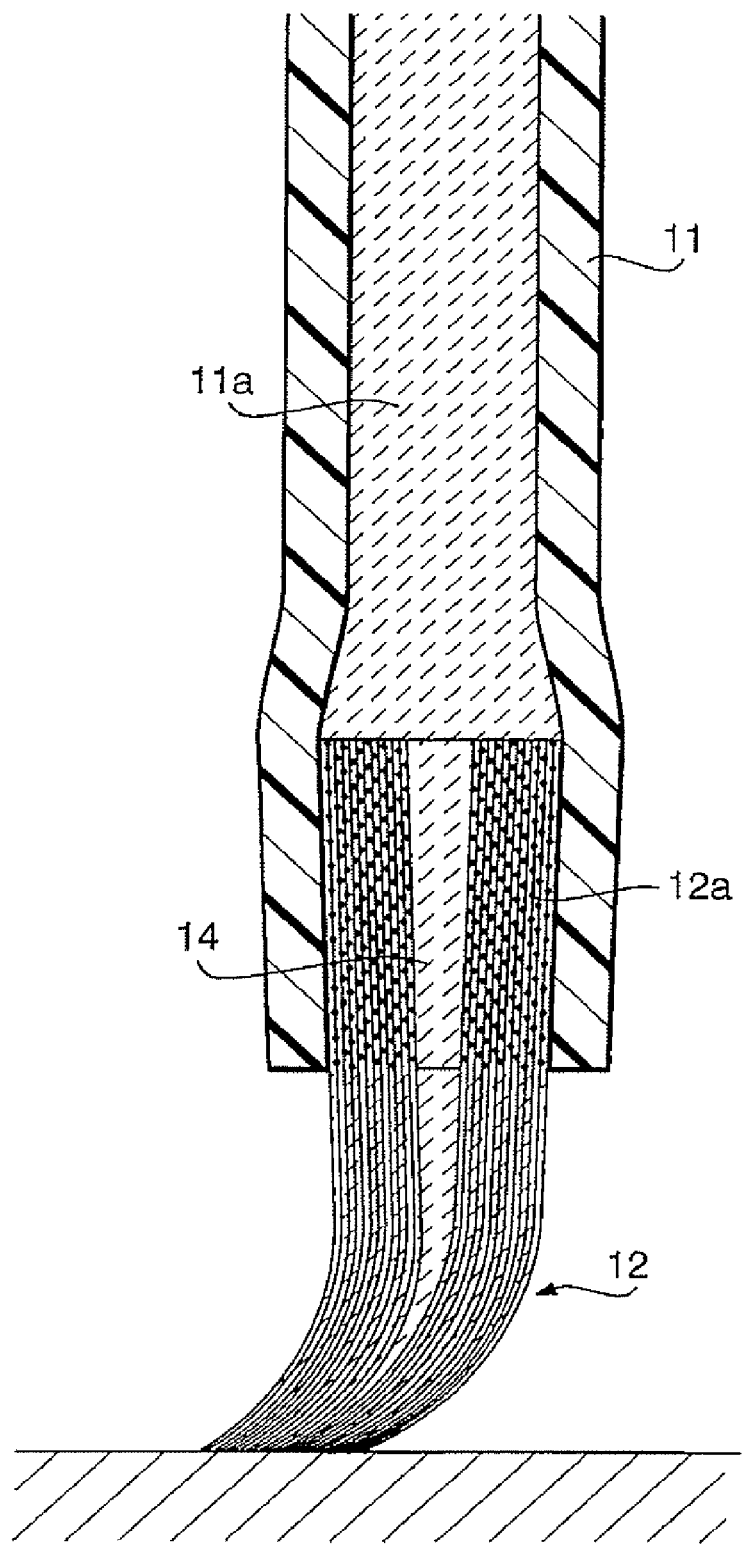
FIG. 5 is a cross-sectional side view of the distal end portion of the liquid applicator for the endoscope in use according to the first embodiment of the present invention.

In the liquid applicator 10 for the endoscope in the embodiment configured as above, the dye solution or the medicinal solution conveyed to the fluid channel 11a of the flexible tube, as shown in FIG. 5, is delivered to the distal end of the pinfeather bundle 12 through the liquid passing opening 14, and penetrates through a gap between each adjacent couple of pinfeathers. Hence, by brushing an in vivo mucous membrane surface with the pinfeather bundle 12, it is possible to apply the dye solution or the medicinal solution thinly (or with desired thickness) in an extremely narrow desired area on the mucous membrane surface.

Figure 7:
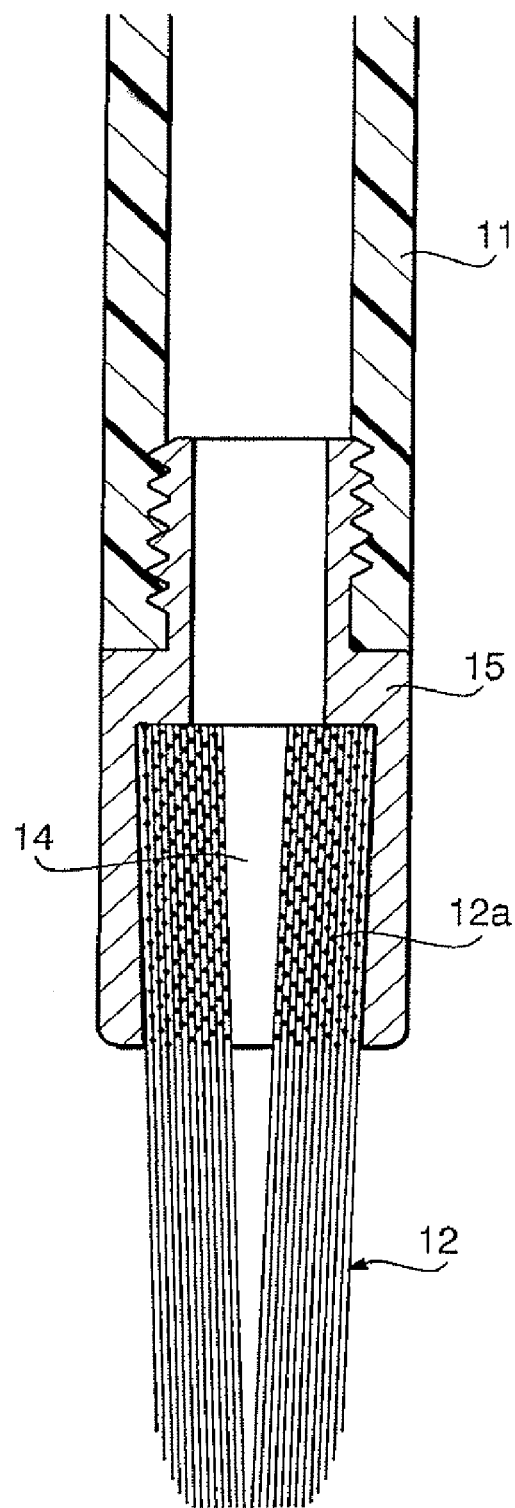
FIG. 7 is a cross-sectional side view of a distal end portion of a liquid applicator for an endoscope according to a second embodiment of the present invention.

It is noted that various sorts of modifications may be possible as far as they are within such a technical scope as not to extend beyond a subject matter of the present invention. For example, as shown in FIG. 7 (a second embodiment), a circumference of the hardened portion 12a of the pinfeather bundle 12 may firmly be fixed to an inner circumference of a tubular pipe sleeve member 15 attached to the distal end of the flexible tube 11. The pipe sleeve member 15 is screwed into the distal end of the flexible tube 11, and is stably fixed thereto.

Figure 8:
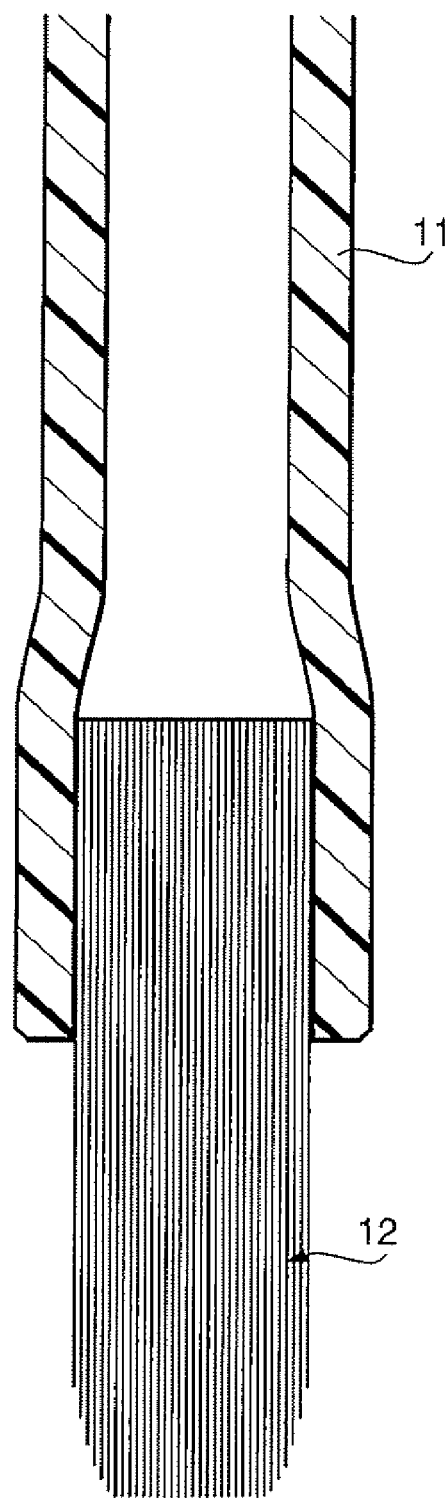
FIG. 8 is a cross-sectional side view of a distal. end portion of a liquid applicator for an endoscope according to a third embodiment of the present invention.
Figure 9:
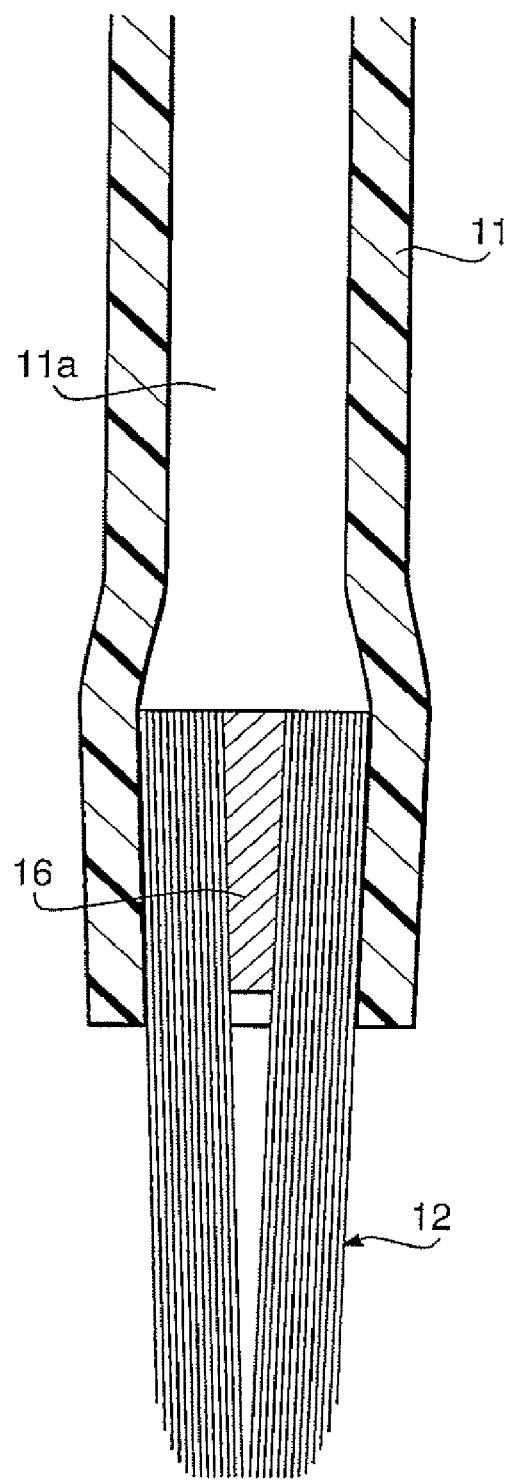
FIG. 9 is a cross-sectional side view of a distal end portion of a liquid applicator for an endoscope according to a fourth embodiment of the present invention.

In addition, as shown in FIG. 8 (a third embodiment), there may be possible as the simplest configuration such a configuration that a number of pinfeathers are bundled into one parallel bundle and are pressed into the distal end of the flexible tube 11 to be fixed thereto without being hardened with the adhesive material. Such a configuration is not as advantageous in that the pinfeather bundle 12 is likely to be easily extracted from the distal end of the flexible tube 11. However, this kind of configuration may be possible in the case where the liquid applicator is used as a disposable one, Further, as shown in FIG. 9 (a fourth embodiment), a convergent tapered core 16 may be arranged on an axis line of a portion of the pinfeather bundle 12 located inside the flexible tube 11, and the pinfeather bundle 12 may be formed to be tapered in conformity to the shape of the convergent tapered core 16 without being hardened with the adhesive material. According to such a configuration, the pinfeather bundle 12 is hard to be extracted even though it is only pressed into the distal end of the flexible tube 11.

It is noted that the present invention is not limited to the aforementioned embodiments. For example, in each of the embodiments, the pinfeather bundle 12 may be formed with a number of pinfeathers being arranged parallel to each other. Further, the liquid storage portion 20 may be provided to be fixed to the rear anchor of the flexible tube 11. In addition, the storage portion 20 or the like my not necessarily be provided.

The present disclosure relates to the subject matter contained in Japanese Patent Application No. P2005-360094, filed on Dec. 14, 2005, which is expressly incorporated herein by reference in its entirety.

What is claimed is:

1. A liquid applicator for an endoscope configured to apply liquid to in vivo tissue, comprising:
   a flexible tube configured to be inserted into and extracted from a treatment tool insertion channel of the endoscope;
   a brush member comprising a plurality of bundled pinfeathers arranged in layers and affixed to each other and on an inside of and protruding distally outward from a distal end of the flexible tube, the brush member formed in a convergent tapered shape and comprising:
      an adhesively hardened portion configured such that the plurality of pinfeathers are affixed to each other throughout the entirety of the hardened portion, the hardened portion ending at the distal end of the flexible tube; and
      a liquid passing opening formed by the hardened portion and which passes through the hardened portion along a center axis line of the brush member; and
   a fluid channel formed in the flexible tube to supply the liquid to the brush member, wherein the flexible tube is longer than the treatment tool insertion channel, wherein a distal end portion of the brush member is in communication with the fluid channel.

2. The liquid applicator according to claim 1, wherein the brush member is configured such that a portion, protruded from the flexible tube, of each of the plurality of pinfeathers can independently bow.

3. The liquid applicator according to claim 1, wherein the brush member is formed to have an external diameter smaller than that of the flexible tube.

4. The liquid applicator according to claim 1, wherein an outer circumference of the hardened portion is fixed to an inner circumference of the flexible tube.

5. The liquid applicator according to claim 1, wherein the brush member is attached to the flexible tube without the hardened portion being protruded from the distal end of the flexible tube.

6. The liquid applicator according to claim 1, further comprising a tubular pipe sleeve member attached to the distal end of flexible tube, wherein an outer circumference of the hardened portion is fixed to an inner circumference of the pipe sleeve member.

7. The liquid applicator according to claim 6, wherein the pipe sleeve member is fixed to the distal end of the flexible tube in a manner screwed thereinto.

8. The liquid applicator according to claim 1, wherein the brush member is pressed into the distal end of the flexible tube to be fixed thereto.

9. The liquid applicator according to claim 8, wherein the brush member is formed with each pinfeather of the plurality of pinfeathers being arranged parallel to an adjacent pinfeather.

10. The liquid applicator according to claim 8, further comprising a convergent tapered core arranged on an axis line of a portion of the brush member located inside the flexible tube, wherein the brush member is formed in a convergent tapered shape.

11. The liquid applicator according to claim 1, further comprising a liquid storage portion provided at a rear anchor side of the flexible tube to pool the liquid to be conveyed to the fluid channel, the liquid storage portion communicating with the fluid channel in the flexible tube.

12. The liquid applicator according to claim 11, wherein the liquid storage portion is detachably provided at the rear anchor side of the flexible tube.

13. The liquid applicator according to claim 11, wherein the liquid storage portion is formed in a pouched shape from resilient material, and wherein the liquid pooled in the liquid storage portion is conveyed to the brush member via the fluid channel by applying a pressing force to the liquid storage portion from an outside thereof.

14. The liquid applicator according to claim 13, wherein the liquid storage portion is formed from rubber material.

15. The liquid applicator according to claim 1, wherein the flexible tube is formed from ethylene tetrafluoride resin.

16. An endoscope comprising:
   a treatment tool insertion channel; and
   a liquid applicator configured to apply liquid to in vivo tissue, comprising:
      a flexible tube insertable into and extractable from the treatment tool insertion channel;
      a brush member comprising a plurality of bundled pinfeathers arranged in layers and affixed to each other and on an inside of and protruding distally outward from a distal end of the flexible tube, the brush member formed in a convergent tapered shape and comprising:
         an adhesively hardened portion configured such that the plurality of pinfeathers are affixed to each other throughout the entirety of the hardened portion, the hardened portion ending at the distal end of the flexible tube; and a liquid passing opening formed by the hardened portion and which passes through the hardened portion along a center axis line of the brush member; and a fluid channel formed in the flexible, wherein the flexible tube is longer than the treatment tool insertion channel, and wherein a distal end portion of the brush member is in communication with the fluid channel.

17. The endoscope according to claim 16, wherein the brush member is configured such that a portion, protruded from the flexible tube, of each of the plurality of pinfeathers can independently bow.

18. The endoscope according to claim 16, wherein the brush member has an external diameter smaller than that of the flexible tube.

19. The endoscope according to claim 16, wherein an outer circumference of the hardened portion is fixed to an inner circumference of the flexible tube.

20. The endoscope according to claim 16, wherein the brush member is attached to the flexible tube without the hardened portion protruded from the distal end of the flexible tube.

21. The endoscope according to claim 16, further comprising a tubular pipe sleeve member attached to the distal end of flexible tube, wherein an outer circumference of the hardened portion is fixed to an inner circumference of the pipe sleeve member.

22. The endoscope according to claim 21, wherein the pipe sleeve member is screwably fixed to the distal end of the flexible tube.

23. The endoscope according to claim 16, wherein the brush member is fixedly press-fit into the distal end of the flexible tube.

24. The endoscope according to claim 23, wherein the brush member is formed with each pinfeather of the plurality of pinfeathers being arranged parallel to an adjacent pinfeather.

25. The endoscope according to claim 23, further comprising a convergent tapered core arranged on an axis line of a portion of the brush member located inside the flexible tube, wherein the brush member has a convergent tapered shape.

26. The endoscope according to claim 23, further comprising a liquid storage portion provided at a rear anchor side of the flexible tube and configured to pool the liquid to be conveyed to the fluid channel, the liquid storage portion communicating with the fluid channel in the flexible tube.

27. The endoscope according to claim 26, wherein the liquid storage portion is detachably connected to the rear anchor side of the flexible tube.

28. The endoscope according to claim 26, wherein:
the liquid storage portion has a pouch shape formed from resilient material; and
the liquid pooled in the liquid storage portion is conveyable to the brush member via the fluid channel by application of a pressing force to the liquid storage portion from an outside of the liquid storage portion.

29. The endoscope according to claim 28, wherein the liquid storage portion comprises an elastomeric material.

30. The endoscope according to claim 16, wherein the flexible tube comprises ethylene tetrafluoride resin.

31. The liquid applicator according to claim 1, wherein the plurality of pinfeathers is arranged in layers in a radial direction of the flexible tube.

32. The endoscope according to claim 16, wherein the plurality of pinfeathers is arranged in layers in a radial direction of the flexible tube.

33. The liquid applicator according to claim 1, wherein all pinfeathers of the plurality of pinfeathers is angled toward the center axis line such that the liquid passing opening distally narrows.

34. The endoscope according to claim 16, wherein all pinfeathers of the plurality of pinfeathers is angled toward the center axis line such that the liquid passing opening distally narrows.

* * * * *